(12) United States Patent
Amsbury et al.

(10) Patent No.: US 7,503,878 B1
(45) Date of Patent: Mar. 17, 2009

(54) POSITION MONITORING DEVICE

(75) Inventors: Burl W. Amsbury, Boulder, CO (US);
Marc R. Silverman, Boulder, CO (US);
Robert M. Holme, Boulder, CO (US);
Susan L. Gerber, Boulder, CO (US);
David W. Herr, Golden, CO (US);
Joshua K. Granof, Louisville, CO (US);
William C. Repenning, Westminster,
CO (US); Michael P. Mellman,
Manhattan Beach, CA (US)

(73) Assignee: Performance Health Technologies, Inc., Boulder, CO (US)

( * ) Notice: Subject to any disclaimer, the term of this patent is extended or adjusted under 35 U.S.C. 154(b) by 521 days.

(21) Appl. No.: 10/834,289

(22) Filed: Apr. 27, 2004

(51) Int. Cl.
*A63B 71/00* (2006.01)

(52) U.S. Cl. .................. 482/9; 482/1; 482/2; 482/3; 482/4; 482/5; 482/6; 482/7

(58) Field of Classification Search ................ 345/156, 345/158; 701/201, 207; 482/1–9, 51, 52, 482/54, 900–902; 434/247
See application file for complete search history.

(56) References Cited

U.S. PATENT DOCUMENTS

| 4,129,125 | A | | 12/1978 | Lester et al. ............ 128/2.05 R |
| 4,757,453 | A | | 7/1988 | Nasiff ..................... 364/415 |
| 4,827,943 | A | | 5/1989 | Bornn et al. ............... 128/668 |
| 4,912,638 | A | * | 3/1990 | Pratt, Jr. .................... 600/595 |
| 5,135,447 | A | | 8/1992 | Robards et al. ............. 482/52 |
| 5,138,154 | A | | 8/1992 | Hotelling ............... 250/231.12 |
| 5,353,793 | A | | 10/1994 | Bornn ..................... 128/642 |
| 5,440,326 | A | | 8/1995 | Quinn .................... 345/156 |
| 5,577,981 | A | * | 11/1996 | Jarvik ...................... 482/4 |
| 5,592,401 | A | * | 1/1997 | Kramer ................... 702/153 |
| 5,667,459 | A | | 9/1997 | Su ............................. 482/4 |
| 5,698,784 | A | | 12/1997 | Hotelling et al. ......... 73/504.16 |
| 5,819,206 | A | * | 10/1998 | Horton et al. .............. 702/150 |
| 5,825,350 | A | | 10/1998 | Case, Jr. et al. ............ 345/163 |
| 5,898,421 | A | | 4/1999 | Quinn ..................... 345/156 |
| 5,899,963 | A | * | 5/1999 | Hutchings ................. 702/145 |
| 5,906,653 | A | * | 5/1999 | Ichimura et al. ............ 701/207 |
| 5,908,396 | A | | 6/1999 | Hayakawa et al. .......... 600/587 |
| 5,913,727 | A | | 6/1999 | Ahdoot ..................... 463/39 |
| 5,980,429 | A | | 11/1999 | Nashner ..................... 482/8 |
| 6,013,007 | A | | 1/2000 | Root et al. .................. 482/8 |
| 6,059,692 | A | * | 5/2000 | Hickman .................... 482/8 |
| 6,119,516 | A | * | 9/2000 | Hock ..................... 73/379.01 |
| 6,358,187 | B1 | | 3/2002 | Smith ....................... 482/4 |

(Continued)

OTHER PUBLICATIONS

Pending U.S. Appl. No. 10/834,324 entitled *Position Monitoring System*; filed Apr. 27, 2004, 58 total pages.

(Continued)

*Primary Examiner*—My-Chau T Tran
(74) *Attorney, Agent, or Firm*—Baker Botts L.L.P.

(57) ABSTRACT

In accordance with one embodiment of the present invention, a device for monitoring a movement of a user includes a sensor module, a processor, and a feedback module. The sensor module is capable of generating positional information describing a movement of a user. The processor is capable of determining based on the positional information that the user has performed a predetermined movement. The feedback module is capable of generating sensory feedback in response to determining that the user has performed the predetermined movement.

26 Claims, 8 Drawing Sheets

U.S. PATENT DOCUMENTS

| | | |
|---|---|---|
| 6,413,190 B1 | 7/2002 | Wood et al. .................... 482/8 |
| 6,463,385 B1 | 10/2002 | Fry ........................... 701/213 |
| 6,511,443 B2 | 1/2003 | Cuce' et al. ................. 600/595 |
| 6,527,711 B1 | 3/2003 | Stivoric et al. ............. 600/300 |
| 6,736,759 B1 | 5/2004 | Stubbs et al. .................. 482/8 |
| 6,774,885 B1 * | 8/2004 | Even-Zohar ................ 345/156 |
| 6,834,436 B2 | 12/2004 | Townsend et al. ............ 33/512 |
| 6,837,827 B1 | 1/2005 | Lee et al. ....................... 482/8 |
| 6,921,351 B1 * | 7/2005 | Hickman et al. ............... 482/8 |
| 7,011,605 B2 | 3/2006 | Shields .......................... 482/8 |
| 7,129,927 B2 * | 10/2006 | Mattsson .................... 345/158 |
| 2003/0163287 A1 * | 8/2003 | Vock et al. .................. 702/187 |
| 2003/0199370 A1 * | 10/2003 | Bucay-Bissu ............... 482/112 |
| 2005/0003931 A1 * | 1/2005 | Mills et al. ..................... 482/5 |

OTHER PUBLICATIONS

Pending U.S. Appl. No. 10/833,830 entitled *Position Monitoring Displays*; filed Apr. 27, 2004, 76 total pages.

* cited by examiner

POSITION MONITORING DEVICE

TECHNICAL FIELD OF THE INVENTION

This invention relates in general to rehabilitation and exercise equipment, and more particularly to a device and method for monitoring movement of a user during exercise.

BACKGROUND OF THE INVENTION

Physical therapy is often prescribed for patients recovering from injury to limbs, joints, muscles and other body parts. The physical therapy process often requires the patient to perform exercises that develop the patient's neuromuscular control of the injured part to regain proprioception and maximal function of the injured part. If the patient, however, does not maintain a proper form or abide by appropriate limits to the range of motion, the benefits of the exercise may be diminished and/or the patient may further injure the relevant body part. As a result, patients may benefit from monitoring to ensure that the exercises are completed in a proper manner. Additionally, because physical therapy can be arduous, tedious, and demoralizing, an exercise program that includes an encouraging and/or entertaining mechanism for providing feedback can improve the effectiveness of the therapy. Moreover, individuals engaged in exercise to improve their general fitness or to develop learned skills, may also benefit from improved forms of feedback.

SUMMARY OF THE INVENTION

In accordance with the present invention, the disadvantages and problems associated physical therapy, fitness exercises, and skill training have been substantially reduced or eliminated. In particular, a system and method are provided for monitoring a movement of a user performing an exercise.

In accordance with one embodiment of the present invention, a device for monitoring a movement of a user includes a sensor module, a processor, and a feedback module. The sensor module is capable of generating positional information describing a movement of a user. The processor is capable of determining based on the positional information that the user has performed a predetermined movement. The feedback module is capable of generating sensory feedback in response to determining that the user has performed the predetermined movement.

In accordance with another embodiment of the present invention, a method for monitoring a movement of a user includes generating positional information. The positional information describes a movement of a user. The method further includes determining based on the positional information that the user has performed a predetermined movement and generating sensory feedback in response to determining that the user has performed the predetermined movement.

Technical advantages of certain embodiments of the present invention include providing feedback that encourages user to develop neuromuscular control of particular body parts and to improve proprioception. Other technical advantages of certain embodiments of the present invention include the ability to teach complex physical skills, the ability to tailor exercise parameters and feedback to suit particular users, the ability to monitor user activity to identify and document the performance of particular movements, and the ability to use this invention with a variety of exercises and body parts.

Other technical advantages of the present invention will be readily apparent to one skilled in the art from the following figures, descriptions, and claims. Moreover, while specific advantages have been enumerated above, various embodiments may include all, some, or none of the enumerated advantages.

BRIEF DESCRIPTION OF THE DRAWINGS

For a more complete understanding of the present invention and its advantages, reference is now made to the following description, taken in conjunction with the accompanying drawings, in which.

DETAILED DESCRIPTION OF THE INVENTION

Figure 1:
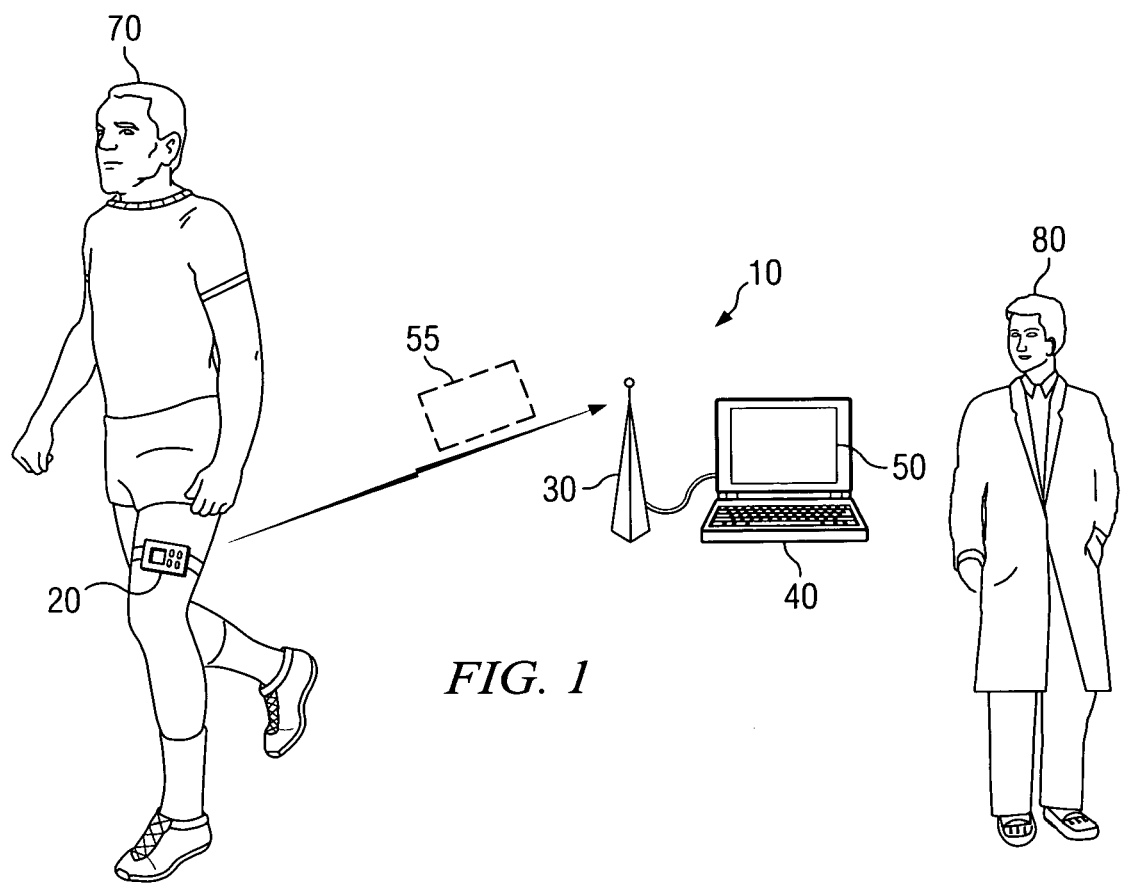
FIG. 1 illustrates a monitoring system according to a particular embodiment.

FIG. 1 illustrates a particular embodiment of a monitoring system 10 that monitors movement of user 70, the movement associated with an exercise performed by user 70. Monitoring system 10 includes a position monitor 20, a receiver 30, a display generator 40, and a display 50. Position monitor 20 generates positional information 55 and transmits positional information 55 wirelessly to receiver 30. Receiver 30 provides positional information 55 to display generator 40, which generates sensory feedback using display 50. By monitoring movement of user 70 and providing sensory feedback based on the movement, monitoring system 10 may increase the effectiveness of exercises user 70 performs as part of physical therapy, a general fitness regiment, or a skill-development program. Additionally, particular embodiments of monitoring system 10 may provide sensory feedback in a manner that is entertaining and/or encouraging for user 70 and, as a result, may induce improved performance by user 70.

Position monitor 20 generates positional information 55 describing movement of user 70 and wirelessly transmits positional information 55 to receiver 30. Position monitor 20 may include any suitable sensors for monitoring the position or movement of user 70 and any appropriate components for communicating information to receiver 30. The contents of a particular embodiment of position monitor 20 are described in greater detail with respect to FIG. 2 below. Additionally, particular embodiments of position monitor 20 may be configured to operate independently of other components of monitoring system 10, as described in greater detail with respect to FIG. 8. In general, position monitor 20 may include any suitable components for monitoring position and/or movement of user 70.

Positional information 55 may represent information describing a linear or rotational position, velocity, acceleration, and/or any other suitable property, state, or characteristic of user 70 that is derived from the position of user 70. Additionally, positional information 55 may describe a position or movement of user 70 in absolute terms and/or by comparison to a reference position or motion or a previous position or motion of user 70. Moreover, positional information 55 may describe the position or movement of user 70 in terms of rotation, translation, or any suitable combination of the two. Furthermore, positional information 55 may describe the position or movement of user 70 generally, a limb or other body part of user 70, a particular portion of the body, clothing, or equipment of user 70, or components attached to or held by user 70. In general, positional information 55 may describe the movement of user 70, or of a portion of the user's body, in any appropriate manner depending on the configuration and characteristics of position monitor 20 and other components of monitoring system 10.

Receiver 30 receives positional information 55 transmitted wirelessly by position monitor 20. Receiver 30 may include an antenna and/or any other components appropriate for receiving wireless communication. Receiver 30 may also include any components appropriate for coupling receiver 30 to display generator 40. Receiver 30 may be capable of receiving information according to 802.11, Bluetooth, or any other suitable wireless communication protocol. Alternatively, receiver 30 may be capable of receiving positional information 55 communicated in a manner that is not in accordance with any communication protocol, such as a stream of values. Receiver 30 may additionally be capable of converting positional information 55 from the wireless communication protocol to a format appropriate for receipt by display generator 40. In general, receiver 30 may include any combination of hardware and/or software suitable for providing the described functionality.

Display generator 40 receives positional information 55 from receiver 30 and, using display 50, provides user 70 sensory feedback based on positional information 55. In a particular embodiment, display generator 40 represents a personal computer (PC) and display 50 represents a computer monitor. In such an embodiment, display generator 40 may receive positional information 55 from receiver 30 and process positional information 55 to generate display information based on positional information 55. Display generator 40 may then communicate display information to display 50, using a conventional interface with display 50, to be used by display 50 in providing user 70 sensory feedback. The contents of display generator 40, according to a particular embodiment, are described in greater detail with respect to FIG. 5 below. In general, display generator 40 may include any combination of hardware and/or software suitable for providing the described functionality. Additionally, as discussed further below, display generator 40 may represent display 50 or elements of display 50 capable of providing the described functionality and display generator 40 and display may represent a single component.

Display 50 receives display information from display generator 40 and displays sensory feedback to user 70. In a particular embodiment, display 50 receives the display information as electric signals generated by display generator 40. Display 50 may provide visual, audio, and/or other appropriate types of sensory feedback based on the display information. Examples of display 50 may include, but are not limited to, computer monitors, television sets, light-emitting diodes (LEDs), and liquid crystal displays (LCDs). In particular embodiments, display generator 40 and display 50 may represent a single integrated device. For example, display generator 40 and display 50 may represent elements of a single laptop computer with the microprocessor of the laptop computer and other appropriate components representing display generator 40 and the screen representing display 50.

In operation, according to a particular embodiment, user 70 prepares for therapy or exercise by affixing position monitor 20 to user 70, grasping position monitor 20, or otherwise attaching position monitor 20 to user 70. For example, as described in greater detail below with respect to FIGS. 3A-3D, position monitor 20 may include a belt, strap, or other component capable of fastening position monitor 20 to user 70. User 70 may attach position monitor 20 to a limb or body part of user 70 using the fastening component. After attaching position monitor 20, user 70 or an operator 80 of monitoring system 10, such as a therapist, trainer, or other party may configure elements of monitoring system 10, as described in greater detail below. After any appropriate configuration, user 70 begins exercising.

While exercising, user 70 moves his or her body or a portion of his or her body, such as a limb, to which position monitor 20 is attached. Position monitor 20 detects the movement of user 70 or the relevant portion of the user's body. For example, in the illustrated embodiment, position monitor 20 is attached to a leg of user 70 and, depending on the configuration of position monitor 20, may be capable of detecting movement of the user's leg, such as when user 70 bends the leg.

Position monitor 20 generates positional information 55 based on the detected movement. As indicated above, positional information 55 may represent information describing a position, velocity, acceleration, and/or any other suitable state, property, or characteristic of user 70 that is derived from the position or movement of user 70. For example, in a particular embodiment, positional information 55 describes movement of user 70 in terms of an angular change in an orientation of position monitor 20 or components of position monitor 20. Position monitor 20 then communicates positional information 55 to receiver 30. Position monitor 20 may generate positional information 55 continuously and transmit the information on a real-time basis. Alternatively, position monitor 20 may monitor the position or movement of user 70 at predetermined intervals and generate and transmit positional information 55 to receiver 30 periodically. In general, position monitor 20 may monitor the position of user 70 at any appropriate time and may transmit positional information 55 at any appropriate time, in conjunction with or independently from, the monitoring.

Position monitor 20 communicates positional information 55 to receiver 30 wirelessly. Position monitor 20 may use any appropriate wireless medium for transmitting positional information 55 including, but not limited to, radio frequency (RF) signals, infrared light, or any other appropriate wireless transmission medium. Additionally, as indicated above, position monitor 20 may transmit positional information 55 in accordance with a suitable wireless communication protocol such as 802.11, Bluetooth, or any other appropriate protocol. Furthermore, position monitor may transmit positional information 55 as a continuous stream, a plurality of discrete messages, a single file, or data structured in any other appropriate manner. Alternatively, position monitor 20 may not be configured to utilize any communication protocols and may instead transmit positional information 55 as a stream of unstructured data.

Receiver 30 receives positional information 55 transmitted by position monitor 20. Receiver 30 may then convert positional information 55 to a form appropriate for communication to display generator 40. In particular embodiments, receiver 30 may also process positional information 55 for communication to display generator 40. For example, if position monitor 20 transmits positional information 55 to receiver 30 as a plurality of messages, receiver may extract and aggregate data from the plurality of messages to reconstruct positional information 55 before transmitting positional information 55 to display generator 40. Receiver 30 then communicates positional information 55 to display generator 40.

Display generator 40 receives positional information 55 from the receiver 30. Display generator 40 may then process positional information 55 in an any appropriate manner to generate the display information from positional information 55. For example, display generator may translate and scale values included in positional information 55 to map the values to a particular portion of display 50. The processing of positional information 55 may further include accessing data stored in a memory of display generator, receiving input from user 70 or operator 80, or any other appropriate steps based on the characteristics and configuration of display generator 40 and, more generally, monitoring system 10. Display generator 40 then transmits the display information to display 50.

Display 50 receives the display information from display generator 40 and generates sensory feedback for user 70 based on the display information. The sensory feedback may include visual, audio, tactile, or any other appropriate form of feedback. The sensory feedback may include any appropriate representation of the user's position and/or movement based on the display information. Additionally or alternatively, the sensory feedback may provide an indication of the user's position and/or movement relative to a goal, a desired motion, or a limit of an exercise being performed by the user.

As one example, display 50 may include a screen and may display on the screen a cursor representing the position of a limb of user 70 to which the position monitor 20 is attached. The cursor may move as user 70 moves the limb during an exercise. Display 50 may also display endpoints of a target range for the exercise which may define, for example, the greatest range of motion through which user 70 can safely move the limb or an optimal range of motion through which user 70 should move the limb to maximize benefits of the exercise. Thus, display 50, in such an embodiment, may provide a visual representation of the position of the limb relative to the endpoints of the target range, and user 70 may use the sensory feedback provided by display 50 to adjust the range of motion that user 70 completes in performing the exercise.

As yet another example, display 50 may include sound generators or components attached to user 70, as part of position monitor 20 or as separate components, that are capable of providing vibrational feedback. Display generator 40 may determine based on positional information 55 that user 70 has performed a prohibited movement and may provide sound or vibrational feedback to indicate user 70 has performed the prohibited movement. As a result, particular embodiments of monitoring system 10 may be used to monitor rehabilitation exercises or other movement of user 70 to ensure that user 70 does not exceed a specified range of motion with an injured limb, execute a harmful combination of movements, perform a particular movement in an ergonomically unsafe manner, or completes any other undesirable movement or series of movements. Position monitor may then indicate that user 70 has performed the undesirable movement. For example, particular embodiments of monitoring system 10 may be used to teach user 70 techniques for performing workplace tasks, such as lifting or carrying heavy objects, in an ergonomically safe manner by providing a particular form of sensory feedback whenever user 70 performs a task incorrectly.

Figure 5:
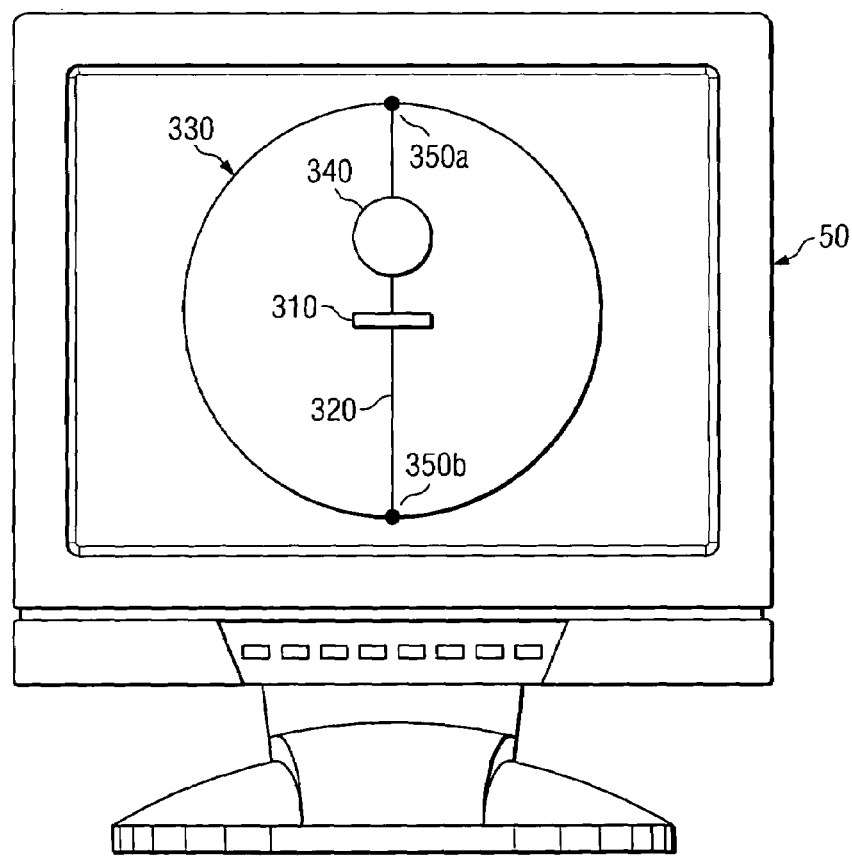
FIG. 5 illustrates operation of a display, according to a particular embodiment, while the monitoring system operates in a particular display mode.
Figure 6:
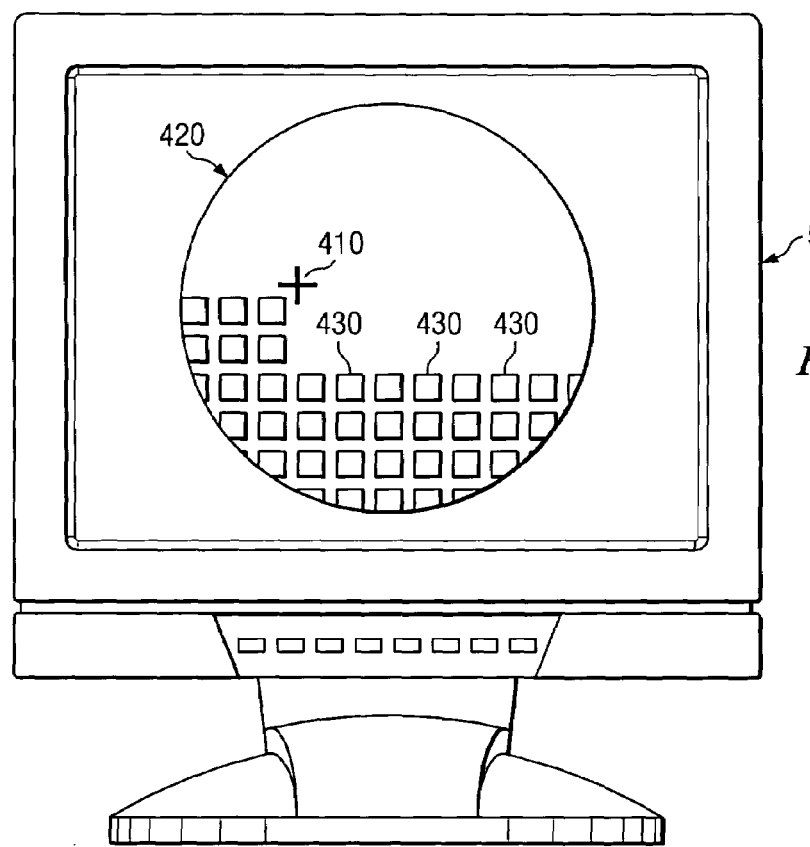
FIG. 6 illustrates operation of the display, according to a particular embodiment, while the monitoring system operates in a particular display mode.
Figure 7:
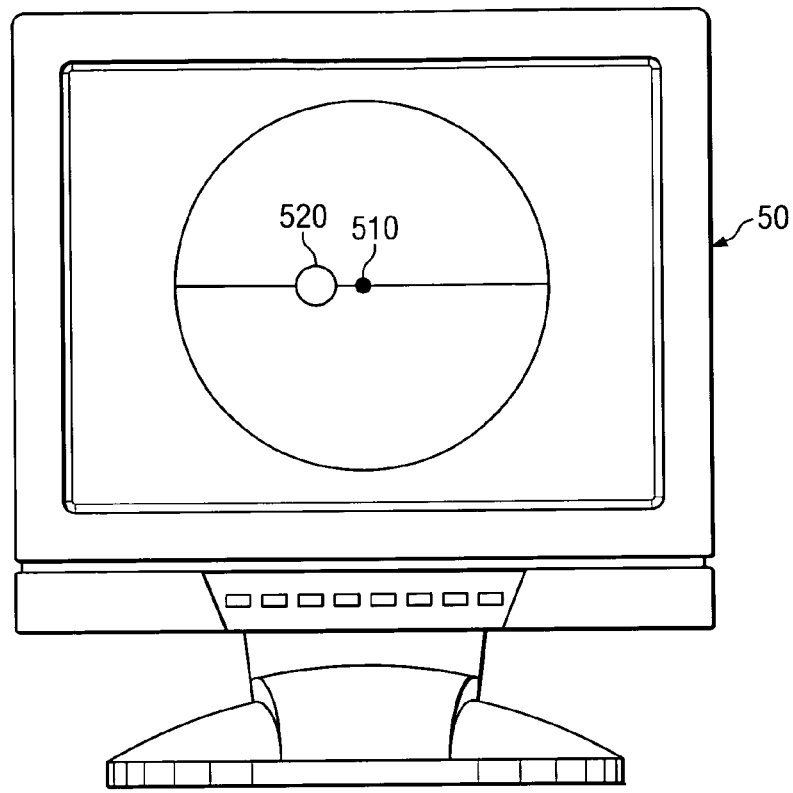
FIG. 7 illustrates operation of the display, according to a particular embodiment, while the monitoring system operates in a particular display mode.

In general, display 50 may include any suitable components for providing sensory feedback to user 70. Furthermore, display generator 40 may generate the display information based, in any suitable manner, on position information 55. Additionally, display 50 may provide sensory feedback, based on the display information, in any appropriate manner. FIGS. 5-7 illustrate in greater detail examples of the sensory feedback provided by particular embodiments of display generator 40 and display 50.

Display generator 40 or other components of monitoring system 10 may also calculate a score 90 for exercises or other physical activity performed by user 70. Score 90 may represent any appropriate measure of how successful user 70 was in satisfying the goal of the exercise or activity, such as a point total, a letter grade, a time measurement, or any other suitable value reflecting an evaluation of the performance of user 70. Display generator 40 may calculate score 90 based on positional information 55 and any other appropriate factors or considerations. Display generator 40 may include score 90 in the display information transmitted to display 50, and display may include score 90 in the sensory feedback presented to user 70, such as by displaying score 90 on a screen of display 50. Additionally or alternatively, display generator 40 may generate a printout that includes score 90 or otherwise communicate score 90 to user 70.

Display generator 40 or other components of monitoring system 10 may also store positional information 55 and/or other data generated based on positional data 55 in a memory. For example, display generator 40 may be capable of storing information identifying a type of exercise performed by user 70, a number of repetitions completed, settings for the exercise, such as a difficulty level, or score 90 for the current exercise. Moreover, monitoring system may be configured to store positional information 55 for multiple users 70. As a result, display generator 50 may store a plurality of user profiles, each user profile containing positional information 55, exercise parameters, or other appropriate information associated with a particular user.

Additionally, as noted above, user 70 or operator 80 may configure monitoring system 10 before or during use. Configuring monitoring system 10 may include loading configuration information from a memory of display generator 40, receiving input to display generator 40, or any other appropriate steps to prepare monitoring system 10 for use. As one example, user 70 may load a user profile associated with user 70 that identifies exercises recommended for user 70, a history of past performances, or any other appropriate information. User 70 may alternatively or additionally load a display profile which defines display parameters for an exercise to be performed by user 70. The display profile may include parameters such as a range of motion for the exercise, computer instructions for generating a particular type of sensory feedback, or any other appropriate information associated with the exercise.

User 70 or operator 80 may utilize a keyboard coupled to display generator 40 or other suitable input devices to configure monitoring system 10. User 70 or the operator may also configure monitoring system 10 using position monitor 20. For example, operator 80 may wear position monitor 20 while demonstrating an exercise for user 70, and display generator 40 may use positional information 55 generated by the operator to determine a range of motion, repetition speed, or other parameters associated with the exercise. Display generator 40 may then store positional information 55 generated during the demonstration for use while user 70 performs the exercise. As another example, the operator may demonstrate a movement, such as a golf swing, a basketball shot, or dance steps, while wearing position monitor 20. Display generator 40 may compare positional information 55 generated by the operator to positional information 55 generated by user 70 to determine how closely user 70 mimicked the motion performed by the operator. As a result, particular embodiments of monitoring system 10 may be used to teach user 70 complex movements associated with particular skills.

Although FIG. 1 illustrates an embodiment of monitoring system 10 that includes a position monitor 20 designed to be worn around a leg of user 70, position monitor 20 may be configured to be worn around any limb, joint, or other appropriate portion of the user's body. Moreover, position monitor 20 may include belts, sleeves, straps, or any other appropriate components for attaching position monitor 20 to user 70. Alternatively, position monitor 20 may be incorporated into clothing or equipment. For example, position monitor 20 may represent a dumbbell handle to which resistance elements, such as weights, elastic bands, or other components may be added to allow for resistance training.

Thus, particular embodiments of monitoring system 10 may facilitate more efficient and safer forms of exercise. As used below, "exercise" or "performing an exercise" may refer to any suitable movements performed as part of physical therapy, fitness programs, and/or skills training. Additionally, particular embodiments of monitoring system 10 may provide a system that is flexible and easily customized to suit the exercise or training needs of a particular user 70. Furthermore, particular embodiments may be easily scaled so that monitoring system 10 can be adjusted to monitor different users 70 and maintain data generated by the multiple users 70.

Figure 2:
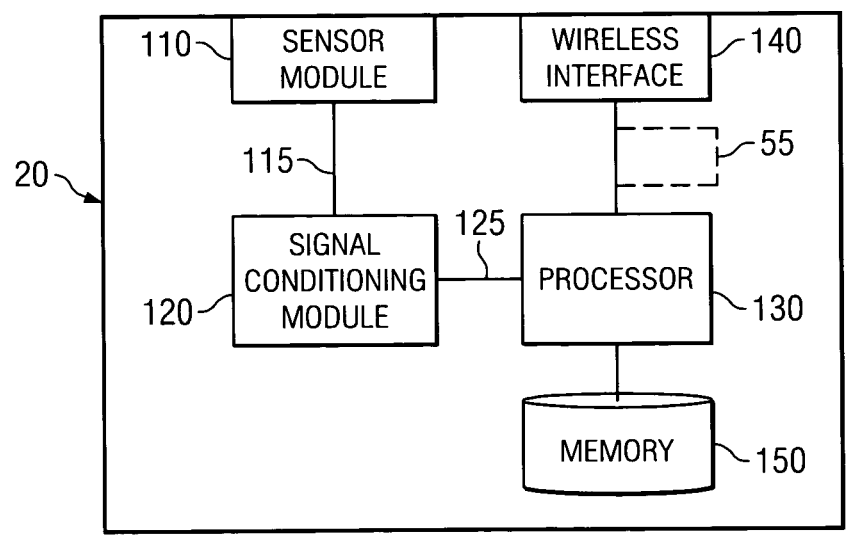
FIG. 2 is a block diagram providing a detailed illustration of a position monitor, according to a particular embodiment.

FIG. 2 is a block diagram providing a detailed illustration of position monitor 20, according to a particular embodiment. In the illustrated embodiment, position monitor 20 includes a sensor module 110, a signal conditioning module 120, a processor 130, a wireless interface 140, and a memory 150. Position monitor 20 generates positional information 55 from movement detected by sensor module 110 and transmits positional information 55 to other components of monitoring system 10 using wireless interface 150.

Housing 100 encloses holds the various components of position monitor 20 and, in particular embodiments, is configured to allow for attachment to user 70 or other components that attach to user 70, as one shown in FIGS. 3A-3D. For the purposes of this description, the housing may "enclose" the components by forming a surface that entirely surrounds the relevant component, by substantially surrounding a portion of the component, or by providing a mounting surface for the component. Thus, components enclosed by housing 100 may be located entirely within housing 100, position partially inside and partially outside housing 100, and/or mounted on the external surface of housing 100. Housing may be composed of plastic, aluminum, or any other suitable material. Housing 100 may also include any suitable mechanical, magnetic, or adhesive mounting elements to attach position monitor 20 to clothing, equipment, or other devices. In a particular embodiment, housing 100 may be shaped and composed of materials to allow user 70 to attach or hold position monitor 20 while performing exercises.

Sensor module 110 detects movement of user 70 holding or wearing position monitor 20 and transmits a sensor output 115 to signal conditioning module 120. Sensor module 110 may include any appropriate components for detecting movement of user 70, such as gyroscopes, accelerometers, global positioning system (GPS) components, or any other suitable sensors. In general, sensor module 110 may include any combination of components, including hardware and/or software, suitable to provide the described functionality. Additionally, as noted above, sensor module 110 may detect movement of user 70 in any appropriate manner. Sensor module 110 may detect a position, velocity, acceleration, and/or any other suitable state, property, or characteristic of user 70 that is derived from the position or movement of user 70. In a particular embodiment, sensor module 110 includes one or more gyroscopes capable of detecting an angular velocity of movement undertaken by user 70. Sensor module 110 generates sensor output 115 as a result of the detected movement. In a particular embodiment, sensor module 110 generates sensor output 115 that represents an analog, electric signal. In general, sensor output 115 may be a signal of any appropriate type.

Signal conditioning module 120 converts, adjusts, reformats, or otherwise modifies sensor output 115 to generate conditioned output 125. For example, sensor module 110 may generate sensor output 115 that represents a velocity of position monitor 20 that signal conditioning module 120 converts to a conditioned output 125 representing a position of position monitor 20. Signal conditioning module may include any components, including hardware and/or software, suitable for formatting sensor output 115. In a particular embodiment, signal conditioning module 120 includes an integrator and an analog-to-digital converter (A/D converter). In general, signal condition module 120 may include any appropriate components, including hardware and/or software, for preparing conditioned output 125 for use by processor 130 or for transmission to receiver 30.

Processor 130 executes instructions associated with the configuration and operation of position monitor 20. Processor 130 may access memory 150 to retrieve and execute stored instructions. Additionally, processor 130 generates positional information 55 from conditioned output 125. Processor 130 may be a microprocessor or other device capable of processing electronic information, including any appropriate controlling logic. Examples of processor 130 include application-specific integrated circuits (ASICs), field-programmable gate arrays (FPGAs), digital signal processors (DSPs) and any other suitable specific- or general-purpose processors. In general, processor 130 may represent one or more physically distinct components and may also provide part or all of the functionality described for sensor module 110, signal conditioning module 120, and/or wireless interface 140.

Wireless interface 140 facilitates communication between position monitor 20 and receiver 30. More specifically, wireless interface 140 transmits positional information 55 and/or other data to receiver 30. Additionally, in particular embodiments, wireless interface 140 may be capable of receiving information from receiver 30 or other components of monitoring system 10. In general, wireless interface 140 may include any appropriate components, such as hardware and/or software, appropriate for communicating information wirelessly to receiver 30 or other components of monitoring system 10.

Memory 150 may store instructions to be executed by processor 130, positional information 55 to be transmitted by wireless interface 140, or any other appropriate information to be provided or used by position monitor 20. Memory 150 may comprise any collection and arrangement of volatile or non-volatile, local or remote devices suitable for storing data, such as for example random access memory (RAM) devices, read only memory (ROM) devices, magnetic storage devices, or any other suitable data storage devices.

In operation, sensor module 110 detects movement of user 70 based on the contents, configuration, and characteristics of sensor module 110, as indicated above. Sensor module 110 generates sensor output 115 based on the detected movement and transmits sensor output 115 to signal conditioning module 120. Signal conditioning module 120 receives sensor output 115 and formats sensor output 115 to be used by processor 130 to generate positional information 55. In a particular embodiment, sensor module 110 generates sensor output 115 as an analog signal representing an angular velocity associated with the user's movement. In such an embodiment, signal conditioning module 120 may generate conditioned output 125 by integrating sensor output 115 and converting the resulting signal to a digital signal. Signal conditioning module 120 then communicates conditioned output 125 to processor 130.

Processor 130 generates positional information 55 from conditioned output 125. As indicated above, positional information 55 describes movement of user 70 in any appropriate manner. Moreover, processor 130, may generate positional information 55 from conditioned output 125 in any appropriate manner. For example, processor 130 may sum, integrate, differentiate, scale, extrapolate, interpolate, or perform any other appropriate computational and/or formatting functions to derive positional information 55 from conditioned output 125. In particular embodiments, processor 130 may communicate conditioned output 125 to wireless transmitter 150 unmodified and positional information 55 may be identical to conditioned output 125. After generating positional information 55, processor 130 communicates positional information 55 to wireless interface 140. Additionally, in a particular embodiment, processor 130 may store positional information 55 in memory 150.

Wireless interface 140 transmits positional information 55 to receiver 30 and/or other components of monitoring system 10. In a particular embodiment, wireless interface 140 includes an antenna capable of transmitting positional information 55. In alternative embodiments, wireless interface 140 may include additional components capable of formatting positional information 55 for transmission to receiver 30. For example, wireless interface 140 may divide positional information 55 into packets, frames, or other data portions suitable for transmission to receiver 30.

FIGS. 3A-3D illustrate embodiments and/or configurations of position monitor 20, specifically position monitors 20a-d, that may be affixed to, held by, or otherwise attached to user 70 in various different manners. In particular, FIGS. 3A-3D show embodiments of position monitor 20a-d that include a belt 350, fastening straps 360, a handle 370, and a sleeve 380, respectively. Although FIGS. 3A-3D illustrate embodiments of position monitor 20 that each attach to user 70 in a particular manner, a particular embodiment of position monitor 20 may, in general, be attached to user 70 in any appropriate manner. Moreover, a particular embodiment of position monitor 20 may include no components capable of attaching position monitor 20 to user 70.

Figure 3A:
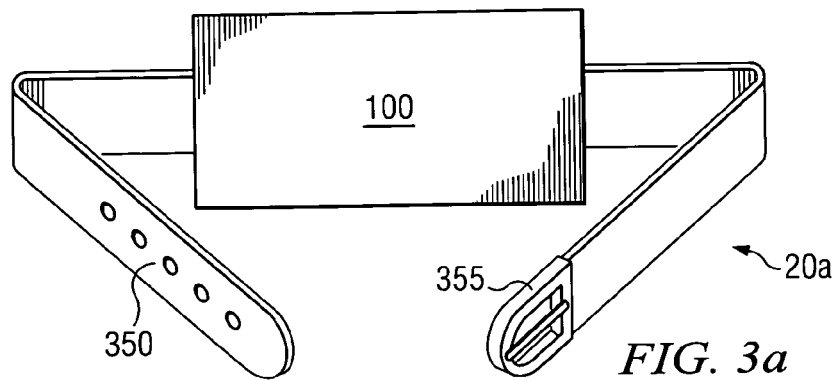
FIG. 3 illustrates configuration of various different embodiments of the position monitor.

FIG. 3A illustrates position monitor 20a that includes belt 350 attached to housing 100. Belt 350 is composed of fabric, flexible plastic, or any other material appropriate for wrapping around the user's body or a designated body part. Belt 350 may be of any suitable shape and/or dimensions. For example, belt 350 may represent a component that is longer than the component is wide, such as a belt configured to wrap around the waist of user 70. As another example, belt 350 may represent a component that is wider than the component is long, such as a component configured to wrap around a leg of user 70 and cover a substantial portion of the length of the leg. Additionally, belt 350 may include one or more fasteners 355 for connecting ends of belt 350 and for holding housing 100 against user 70. Fastener 355 may represent a buckle, buttons, a hook-and-loop strip (such as Velcro™), or any component appropriate for connecting the ends of belt 350 in a manner suitable to keep housing 100 attached to user 70. Alternatively, fastener 355 may represent a knot tied from ends of belt 350.

Figure 3B:
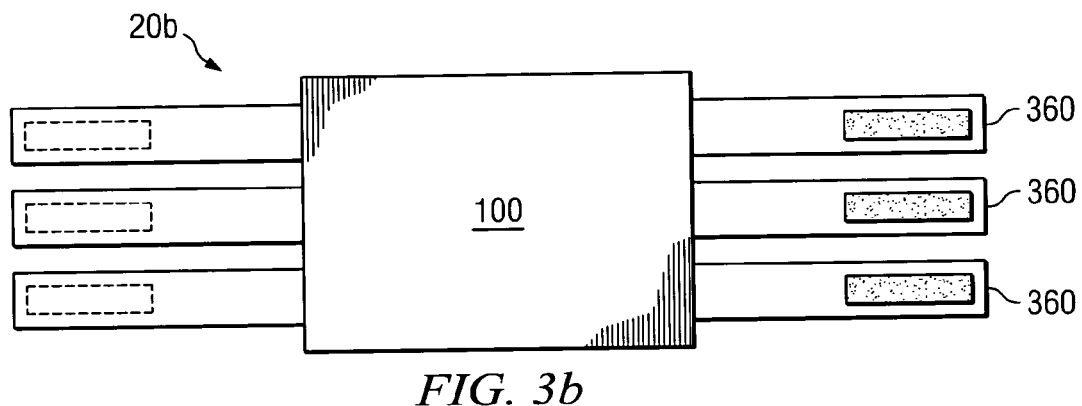

FIG. 3B illustrates position monitor 20b that includes one or more fastening straps 360 that adhere to user 70, clothing or equipment of user 70, or other devices used by user 70 during exercise. Fastening straps 360 may be composed of fabric, plastic, metal, and/or any other suitable material with adhesive properties. Examples of fastening straps 360 may include cloth treated with chemical adhesives, hook-and-loop strips, or magnetized metal pieces. In general, the adhesive qualities of fastening straps 360 may be based on chemical, physical, magnetic, or any other suitable properties of fastening straps 360.

Figure 3C:
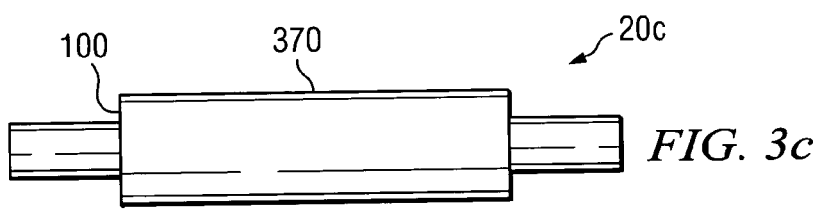

FIG. 3C illustrates position monitor 20c that includes handle 370 that user 70 may use to hold position monitor 20c. Handle 370 may be composed of any appropriate material and may be shaped in any form suitable for user 70 to hold during exercise. Additionally, as shown in FIG. 3, handle 370 may be capable of holding or connecting to weights, elastic bands, exercise equipment (such as weight machine cables), or other resistive elements so that user 70 may use position monitor 20c as part of resistance training. Handle 370 may represent a portion or all of housing 100, or may represent an entirely separate component or components.

Figure 3D:
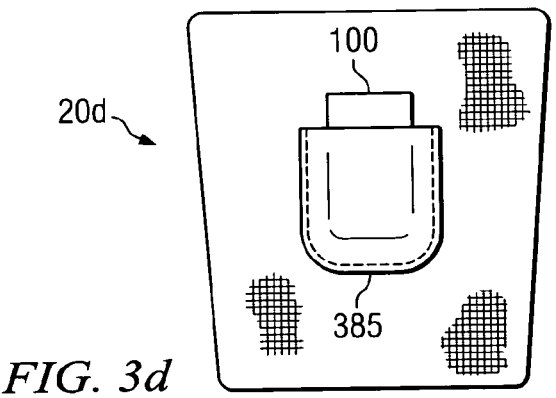

FIG. 3D illustrates position monitor 20d that includes sleeve 380. Sleeve 380 composed of any elastic material capable of being stretched or otherwise deformed so that user 70 may position sleeve 380 over a particular body part. After being positioned, the elastic material of sleeve 380 is then capable of grasping the relevant body part in a manner suitable to allow user 70 to exercise while wearing sleeve 380. Additionally, sleeve 380 may include pocket 385. Pocket 385 may represent any pocket, pouch, cavity, or other feature of sleeve 380 suitable for holding position housing 100 during exercise. Pocket 385 may completely enclose housing 100 or partially enclose housing 100 so that housing 100 may be inserted and removed as desired. Additionally, sleeve 380 may be designed to fit a particular part of the user's body and position monitor 20d may include multiple sleeves 380 designed to fit different parts of the user's body.

Figure 4:
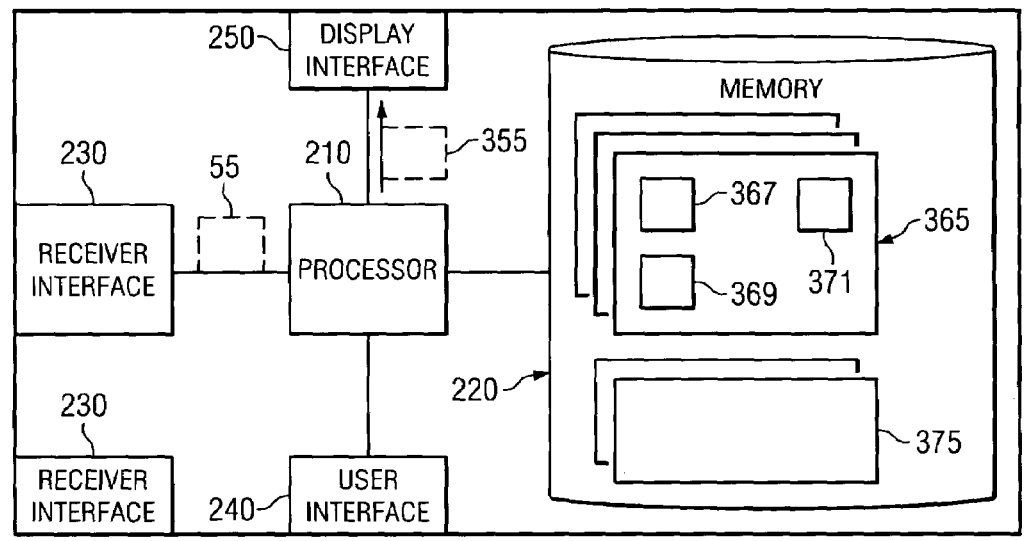
FIG. 4 is a block diagram providing a detailed illustration of a display generator, according to a particular embodiment.

FIG. 4 illustrates display generator 40 according to a particular embodiment. Display generator 40 includes a processor 210, a memory 220, a receiver interface 230, a user interface 240, and a display interface 250. Display generator 40 receives positional information 55 from receiver 30 through receiver interface 230 and generates, based on positional information 55, display information 355 to be transmitted to display 50 through display interface 250.

Processor 210 executes instructions associated with the configuration and operation of display generator 40. Processor 210 may access memory 220 to retrieve and execute stored instructions. Additionally processor 210 generates display information 355 from positional information 55. Processor 210 may be a microprocessor or other device capable of processing electronic information, including any appropriate controlling logic. Examples of processor 210 include application-specific integrated circuits (ASICs), field-programmable gate arrays (FPGAs), digital signal processors (DSPs) and any other suitable specific- or general-purpose processors. In general, processor 210 may represent one or more physically distinct components and may also provide part or all of the functionality described for display interface 250, receiver interface 230, and user interface 240.

Memory 220 may store instructions to be executed by processor 210, display information 355 to be transmitted to display 50, user profiles 365, display profiles 375, or any other appropriate information to be provided or used by display generator 40. Memory 220 may comprise any collection and arrangement of volatile or non-volatile, local or remote devices suitable for storing data, such as for example random access memory (RAM) devices, read only memory (ROM) devices, magnetic storage devices, optical storage devices, or any other suitable data storage devices.

Receiver interface 230, user interface 240, and display interface 250 facilitate communication between display generator 40 and display 50, receiver 30, and user 70 (or operator 80), respectively. Each of display interface 250, receiver interface 230, and user interface 240 may include any components appropriate for providing the functionality described. Furthermore, display interface 250, receiver interface 230, and user interface 240 may each represent a single component or any number of separate components, including shared components common to display interface 250, receiver interface 230, and/or user interface 240. Moreover, in particular embodiments, processor 210 may represent a component of display interface 250, receiver interface 230, and/or user interface 240. In a particular embodiment, display generator 40 and display 50 represent elements of a conventional laptop computer. In such an embodiment, display interface 250 may represent internal circuitry and hardware connecting computing elements of the laptop, such as processor 210, with a screen of the laptop computer. Additionally, in such an element, receiver interface 230 may represent an input port capable of receiving data from receiver 30, while user interface 240 may represent a keyboard and/or mouse of the laptop computer.

In operation, display generator 40 receives positional information 55 from receiver 30 through receiver interface 230. Display generator 40 may then process positional information 55 in an appropriate manner, based on the characteristics and configuration of monitoring system 10, to produce display information 355. Display information 355 represents any type of signals transmitted to display 50 by display generator 40 suitable to cause display 50 to generate sensory feedback. In a particular embodiment, display information 355 represents conventional video and/or audio signals appropriate for transmission to a computer monitor or laptop screen.

Additionally, in particular embodiments, user 70 or operator 80 may configure display generator 40 prior to or during use. To configure display generator 40, user 70 or operator 80 may utilize user interface 240, such as by typing on a keyboard of user interface 240, or position monitor 20, such as by moving position monitor 20 to define parameters of an exercise. In general, user 70 or operator 80 may configure display generator 40 in any appropriate manner depending on the characteristics of display generator 40 and/or other components of monitoring system 10.

As one example, user 70 or operator 80 may configure display generator 40 by loading a user profile 365 from memory 220. In a particular embodiment, user profiles 365 include user data 367, exercise data 369, and historical data 371. User data 367 may include information such as a name, age, height, weight, arm span, injury description, or any other suitable information that identifies or describes user 70. Exercise data 369 identifies a prescribed exercise or exercise program for user 70. Exercise data 369 may include a list of exercises, a recommended range of motion for one or more exercises, a previously used range of motion for these exercises, a display profile 375 or display mode associated with an exercise, information describing a model motion (such as a golf swing), or any other information describing one or more exercises associated with user 70. User profile 365 may also include historical data 371 for user 70 including a total number of repetitions user 70 has performed of a particular exercise, a maximum range motion exhibited by user 70 during previous exercise sessions, a maximum weight utilized by user 70 with a particular exercise, a highest score 90 achieved by user 70 for a particular exercise, or any other suitable information describing a previous performance or performances of user 70. In general, user profile 365 may include any appropriate information associated with user 70 that may be used by display generator 40 or displayed by display 50 during operation.

As another example, user 70 or operator 80 may configure display generator 40 by loading a display profile 375. Display profile 375 may include any suitable information to define a display mode associated with an exercise to be performed by user 70. The display mode may define or describe the manner in which display generator 40 generates display information 355 from positional information 55 and may determine, at least in part, the resulting sensory feedback provided by display 50. For example, display profile 375 may specify that display generator 40 generate display information 355 so that movement of user 70 is shown on display 50 by moving a position cursor along a vertical axis. Additionally, display profile 375 may indicate, based on the specified display mode or other information in display profile 375, a method by which display generator 40 determines a score for user 70 for a particular exercise. FIGS. 5-7 provide more detailed examples of the sensory feedback provided by particular embodiments of monitoring system 10 while operating in particular display modes. Display profile 375 may include data used by processor 210 to set a display mode for monitoring system 10, computer instructions implementing a particular display mode, or any other suitable information specifying the manner in which processor 210 generates display information 355 from positional information 55.

FIGS. 5-7 illustrate sensory feedback provided by particular embodiments of display 50 while monitoring system 10 is operating in various example display modes. A particular embodiment of monitoring system 10 may be capable of implementing one or more display modes. Moreover, the display mode implemented by a particular embodiment of monitoring system 10 may be a fixed characteristic of that embodiment or may be configured by user 70 or operator 80 prior to or during use. The descriptions below assume that display 50 represents a computer screen or other device capable of providing visual feedback to user 70. Although, as indicated above, display 50 may provide sensory feedback that includes visual, audio, tactile, or any other appropriate form of sensory feedback, the descriptions below focus on visual feedback provided by display 50 during operation. Furthermore, particular embodiments of display 50 may provide additional forms of feedback while operating in the described display modes.

FIG. 5 illustrates sensory feedback provided by a particular embodiment of display 50 while monitoring system 10 is operating in a particular display mode. For the purposes of this illustration, this display mode will be referred to as "monitor mode." For the sake of simplicity, this description may refer to display generator 40 as "moving" or "displaying" elements of FIG. 5. In particular embodiments, display generator 40 may "move" or "display" these elements by generating display information 355 that causes display 50 to move or display these elements.

While operating in monitor mode, display generator 40 generates display information 355 that causes display 50 to display a position cursor 310, a target path 320, and an target range 330. Position cursor 310 monitors movement of user 70. Target path 320 represents a range of motion associated with an exercise to be performed by user 70. Although FIG. 5 illustrates an embodiment of monitoring system 10 that displays a linear target path 320, particular embodiments of monitoring system 10 may be configured to detect motion of user 70 along multiple axes. As a result, in such embodiments, target path 320 may comprise a two-dimensional element, such as a curved target path 320, or a three-dimensional element.

Additionally, display 50 may display a pacing target 340. Moreover, in particular embodiments in which display generator 40 displays pacing target 340, target path 320 may be defined by the movement of pacing target 340 and display generator 40 may not provide additional visual indication of target path 320. In such an embodiment, user 70 may perform the exercise with the goal of following the movement of pacing target 340.

In a particular embodiment, display generator 40 moves position cursor 310 in response to movement by user 70. As noted above, while monitoring system 10 is operating in monitor mode, user 70 may perform an exercise with a goal of moving position cursor 310 along target path 320. If display generator 40 displays pacing target 340, user 70 may additionally or alternatively perform the exercise with a goal of keeping position cursor 310 within pacing target 340 as pacing target 340 moves along target path 320. Thus, user 70 may adjust his or her movement to respond to a length or shape of target path 320 and/or to movement of pacing target 340.

In a particular embodiment, as shown in FIG. 5, display generator 40 displays position cursor 310 as a horizontal bar, target path 320 as a linear element connecting points 350*a* and 350*b* on exercise range 330, pacing target 340 as a shaded circle, and exercise range 330 as a circular outline. Display generator 40 may, however, display position cursor 310, pacing target 340, and exercise range 330 in any appropriate form. Additionally, for the purposes of this illustration, this description assumes that position monitor 20 and, more generally, monitoring system 10 are configured to detect movement of user 70 along only a single axis. As indicated above, however, particular embodiments of monitoring system 10 may be able to detect movement along multiple axes and provide sensory feedback based on movement along these multiple axes.

While monitoring system 10 is operating in the monitor mode, user 70 or operator 80 may configure display generator 40 to define a movement range associated with target path 320. The movement range represents a range of motion for an exercise to be performed by user 70 and may be used by display generator 40 to define target path 320. In a particular embodiment, display generator 40 may then associate the boundary of exercise range 330 with the extremes of target path 320. Thus, points 350*a* and 350*b* on the boundary of exercise range 330 may represent the extremes of the range of motion the user moves through while performing the exercise. In general, however, display generator 40 may mark the endpoints of target path 320 in any appropriate manner on or within the boundary of exercise range 330. User 70 or operator 80 may define the movement range by entering values through user interface 240, by moving position monitor 20 through this movement range during configuration, by loading a user profile 365, or in any other suitable manner. User 70 or operator 80 may additionally configure display generator 40 by defining a speed for pacing target 340, an exercise time, a number of repetitions, an angle at which the exercise will be performed, and/or a difficulty level for the exercise, or by setting any other suitable parameters.

After user 70 or operator 80 configures display generator 40, display generator 40 begins moving position cursor 310 in response to movement of user 70, based on positional information 55. In a particular embodiment, display generator 40 also moves pacing target 340 across target path 320. Display generator 40 may move pacing target 340 continuously, at a constant or variable rate, or intermittently, stopping periodically. Furthermore, display generator 40 may move pacing target 340 based on a speed set during configuration.

Additionally, display generator 40 may determine score 90 for user 70 based on how successfully user 70 achieved the goal of the exercise. Score 90 may represent any appropriate measure of how successful user 70 was in satisfying the goal, such as a point total, a letter grade, a time measurement, or any other suitable value. As one example, display generator 40 may generate a score that represents an amount of time that position cursor 310 was positioned within a predetermined range from target path 320 or pacing target 340. In this case, display generator may start a timer whenever user 70 is able to position cursor 310 within the predetermined range from target path 320 or pacing target 340 and may stop the time whenever the movement of user 70 causes the position of position cursor 310 to fall outside the predetermined range. As a result, score 90, in this example, represents the total amount of time the position cursor 310 was located within the predetermined range from target path 320 during the exercise. Alternatively, display generator 40 may determine score 90 based on the percentage of target path 320 which position cursor 310 traverses during the exercise. If display generator 40 also displays pacing target 340, display generator 40 may also determine score 90 based on how successful user 70 was in following pacing target 340. For example, display generator 40 may generate score 90 that represents an amount of time that position cursor 310 was positioned within pacing target 340 as pacing target 340 traverses target path 320. In general, display generator 40 may determine score 90 based on any appropriate factors or considerations. Display generator 40 may then display score 90 on display 50, print a report containing score 90, save score 90 in a particular user profile 365 associated with user 70, or provide score 90 to user 70 in any other suitable manner.

Thus, while operating in monitor mode, monitoring system 10 may encourage user 70 to exercise neuromuscular control of the relevant limb or body part in an effort to mimic the movement of pacing target 340. Additionally, the sensory feedback provided by monitoring system 10 may develop or improve the user's proprioception, his or her ability to sense the position, location, orientation, and/or movement of the relevant body part. As a result, particular embodiments of monitoring system 10 operating in monitor mode may produce improved results when used during physical therapy and other types of exercises. Furthermore, because particular embodiments of monitoring system 10 operating in monitor mode may encourage and assist user 70 in performing complex movements, feedback provided by monitor mode may assist in teaching learned skills that involved particular forms of movement, such as a golf swings, basketball shots, bat swings, dance steps, or any other appropriate skill. Additionally, by providing a measurable goal and/or generating a score based on the performance of user 70, particular embodiments of monitoring system 10 may provide feedback that is entertaining and/or encouraging to user 70.

FIG. 6 illustrates sensory feedback provided by a particular embodiment of display 50 while monitoring system 10 is operating in a particular display mode. For the purposes of simplicity, this display mode will be referred to as "coverage mode." While operating in coverage mode, display generator 40 displays a position cursor 410, a target area 420, and coverage points 430. More specifically, display generator 40 displays coverage points 430 to indicate areas within target area 420 over which user 70 has moved position cursor 410. In a particular embodiment, as shown in FIG. 6, display generator 40 displays position cursor 410 as a set of crosshairs, target area 420 as a circular outline, and coverage points 430 as shaded squares. Display generator 40 may, however, display position cursor 410, target area 420, and coverage points 430 in any appropriate form. For example, in a particular embodiment of monitoring system 10, display 50 represents a screen of a computer monitor. In such an embodiment, coverage points 430 may represent individual pixels of display 50, multi-pixel blocks, other multi-pixel shapes, or any other suitable grouping of pixels.

While monitoring system 10 is operating in the coverage mode, user 70 or operator 80 may configure display generator 40 to define target area 420. Target area 420 may represent a desired range of motion for an exercise to be performed by user 70. Additionally, for the purposes of this illustration, this description assumes that position monitor 20 and, more generally, monitoring system 10 are configured to detect movement of user 70 along only two axes. Target area 420 may thus represent, for example, a range of motion appropriate for an arm of user 70 relative to the associated shoulder socket. User 70 or operator 80 may define the target area 420 by drawing a shape with a component of user interface 240, such as a light pen, by drawing target area 420 through the movement of position monitor 20, by loading a user profile 365 that defines a shape for target area 420, or in any other suitable manner. User 70 or operator 80 may additionally configure display generator 40 by defining an exercise time, a number of repetitions, a size for coverage points 430, a shape for coverage points 430, a starting point for position cursor 410, an angle at which the exercise will be performed, a percentage goal indicating a desired percentage of target area 420 to be covered during the exercise, and/or a difficulty level for the exercise, or by setting any other appropriate parameters.

After user 70 or operator 80 configures display generator 40, display generator 40 monitors movement of position monitor 20 and moves position cursor 410 based on the movement of position monitor 20. When display generator 40 moves position cursor 410 to a new position, display generator 40 displays a coverage point 430 in the previous position of cursor position 410. As a result, coverage points 430 displayed by display generator 40 may indicate the range of motion through which user 70 has moved the relevant limb or body part.

While monitoring system is operating in coverage mode, user 70 may perform an exercise with a goal of filling all or a predetermined portion of target area 420 with coverage points 430. Additionally, display generator 40 may determine score 90 for user 70 based on how successfully user 70 achieved this goal. As one example, display generator 40 may generate score 90 based on an amount of time required by user 70 to completely cover target area 420 with coverage points 430, a percentage of target area 420 covered by coverage points 430 at the expiration of a predetermined time period, or any other appropriate considerations or factors. Display generator 40 may then display score 90 on display 50, print a report containing score 90, save score 90 in user profile 365 associated with user 70, or provide score 90 to user 70 in any other suitable manner.

Thus, while operating in coverage mode, monitoring system 10 may encourage user 70 to move the relevant body part through a predetermined range of motion. As a result, particular embodiments of monitoring system 10 operating in monitor mode may produce improved results when used during physical therapy and other types of exercises. Additionally, by providing a measurable goal and/or generating a score based on the performance of user 70, particular embodiments of monitoring system 10 may provide feedback that is entertaining and/or encouraging to user 70.

FIG. 7 illustrates sensory feedback provided by a particular embodiment of display 50 while monitoring system 10 is operating in a particular display mode. For the purposes of simplicity, this display mode will be referred to as "challenge mode." While operating in challenge mode, display generator 40 generates a model of a naturally unstable system, using positional information 55 as an input to the system. According to a particular embodiment of monitoring system 10, user 70 may attempt to maintain a stable state by adjusting the position of a monitored body part to respond to system perturbations generated by display generator 40. For example, display generator 50 may model a system that includes an inverted pendulum that responds to random perturbations generated by display generator 40. Display generator 40 may model movement of user 70 as a force applied to the fulcrum of the pendulum with the magnitude of the force determined based on positional information 55. User 70 may thus attempt to stabilize the system through movement of the relevant body part.

User 70 or operator 80 may configure display generator 40 before user 70 begins exercising. For example, user 70 or operator 80 may access a display profile 375 that includes stored values for parameters of the model such as friction, air resistance, gravity, or any other values appropriate for use in the model. As another example, user 70 or operator 80 may provide input to display generator 40 through user interface 760 that includes values for model parameters of the model.

During operation, display 50 displays output icon 510 and position target 520. More specifically, display generator 40 monitors movement of user 70 and uses positional information 55 as an input to the unstable system. Output icon 510 reflects a measure of an output value of the unstable system. Once user 70 begins exercising, display generator 40 updates the position of output icon 510 as the output value fluctuates in response to changes in positional information 55. Additionally, display generator 40 may move position target 520. Display generator 40 may move position target 520 continuously, at a constant or variable rate, or intermittently, stopping periodically. Furthermore, display generator 40 may move position target 520 based on a speed or other parameters set during configuration. User 70 may attempt to control the position of output icon 510 relative to position target 520 in accordance with a goal of the exercise.

For example, as noted above, display generator may model an inverted pendulum. Display generator 40 may monitor movement of user 70 through positional information 55. Display generator 40 may determine, based on positional information 55, a force to apply to the fulcrum of the pendulum in the model. Display generator 40 may then determine an output value, in this case a measure of a displacement of the arm of the pendulum based upon positional information 55 and the model parameters, which may include values for friction, pendulum mass, pendulum length, gravity, and other appropriate parameters Display generator 40 may then provide user 70 feedback on this output value by moving output icon 510 on display 50. Although this description illustrates operation of a particular embodiment of display generator 40 modeling a particular unstable system, display generator 40 may, in general, use any appropriate dynamic system to generate the position for output icon 510. While monitoring system is operating in challenge mode, user 70 may perform an exercise with a goal of maintaining a particular position for output icon 510. Additionally, display generator 40 may determine score 90 for user 70 based on how successfully user 70 achieved this goal. As one example, display generator 40 may generate score 90 based on an amount of time during which user 70 maintained the position of output icon 510 within position target 520. Display generator 40 may then display score 90 on display 50, print a report containing score 90, save score 90 in user profile 365 associated with user 70, or provide score 90 to user 70 in any other suitable manner.

Thus, while operating in challenge mode, monitoring system 10 may encourage user 70 to exercise neuromuscular control of the relevant body part. As a result, particular embodiments of monitoring system 10 operating in challenge mode may produce improved results when used during physical therapy and other types of exercises. Additionally, by providing a measurable goal and/or generating a score based on the performance of user 70, particular embodiments of monitoring system 10 may provide feedback that is entertaining and/or encouraging to user 70. Furthermore, because of the complex interaction between movement of output icon 510 and position target 520, particular embodiments of monitoring system 10 operating in the challenge mode may provide feedback that encourages user 70 to be more conscientious of the movements executed by user 70 in performing the exercise and that, as a result, encourages greater precision on the part of user 70. Moreover, the sensory feedback provided by monitoring system 10 may also develop or improve the user's proprioception.

Figure 8:
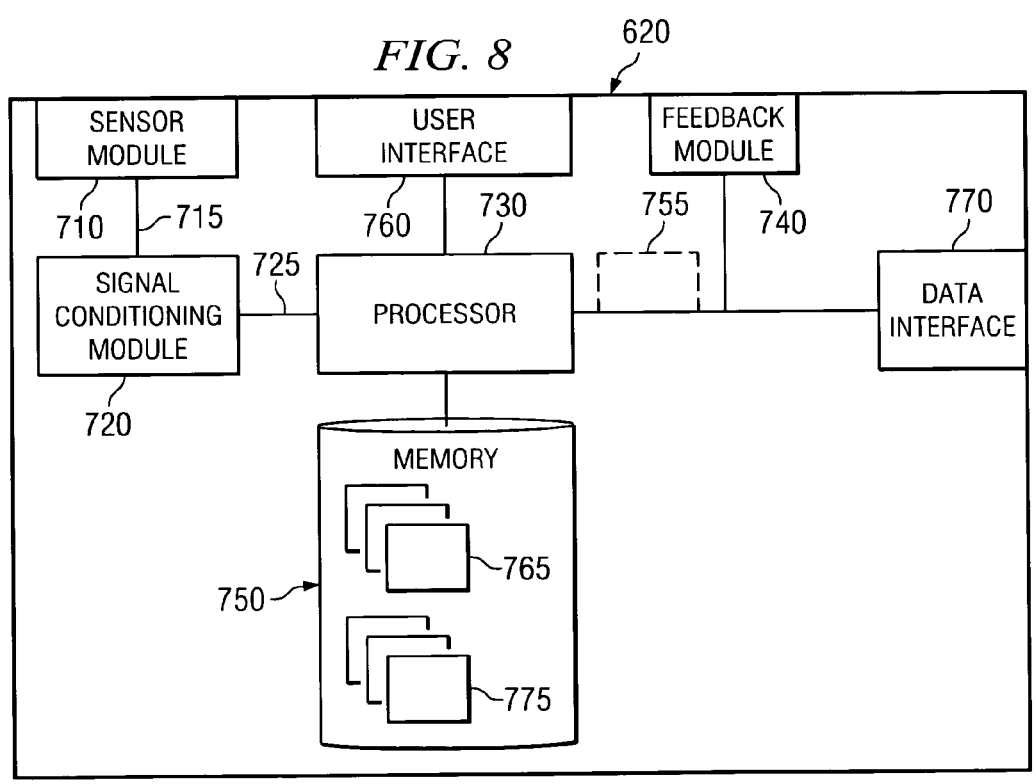
FIG. 8 is a block diagram providing a detailed illustration of a standalone position monitor according to a particular embodiment.

FIG. 8 illustrates a particular embodiment of position monitor 20, standalone monitor 620, configured to operate independently of other components of monitoring system 10. Standalone monitor 620 includes a sensor module 710, a signal conditioning module 720, a processor 730, a feedback module 740, a memory 750, a user interface 760, and a data interface 770. Standalone monitor 620 detects movement of user 70 and, if user 70 performs a critical movement, provides feedback to user 70. In a particular embodiment, standalone monitor 620 may represent an embodiment of position monitor 20 that includes particular hardware and/or software.

Sensor module 710 detects movement of a user 70 holding or wearing standalone monitor 620 and transmits a sensor output 715 to signal conditioning module 120. Sensor module 710 may include any appropriate components for detecting movement of user 70, such as gyroscopes, accelerometers, global positioning system (GPS) components, or any other suitable sensors. In general, sensor module 710 may include any combination of components, including hardware and/or software, suitable to provide the described functionality.

Additionally, sensor module 710 may detect movement of user 70 in any appropriate manner. Sensor module 710 may detect a position, velocity, acceleration, and/or any other suitable state, property, or characteristic of user 70 that is derived from the position or movement of user 70. In a particular embodiment, sensor module 710 includes one or more gyroscopes capable of detecting an angular velocity of motion undertaken by user 70. Sensor module 710 generates sensor output 715 as a result of the detected movement. In a particular embodiment, sensor module 710 generates sensor output 715 that represents an analog, electric signal. In general, sensor output may be a signal of any appropriate type.

Signal conditioning module 720 converts, adjusts, reformats, or otherwise modifies sensor output 715 to generate conditioned output 725. Signal conditioning module may include any components, including hardware and/or software, suitable for formatting sensor output. In a particular embodiment, signal conditioning module 720 includes an integrator and an analog-to-digital converter (A/D converter). In general, signal conditioning module 720 may include any appropriate components, including hardware and/or software, for preparing conditioned output 725 for use by processor 730.

Processor 730 executes instructions associated with the configuration and operation of standalone monitor 620. Processor 730 may access memory 750 to retrieve and execute stored instructions. Additionally, processor 730 determines, based on positional information 755, whether user 70 has performed a critical movement. The critical movement may represent any predetermined movement of user 70 that is appropriate for detection by sensor module 710. For example, if sensor module 710 is capable of detecting movement along a single axis, the critical movement may represent any movement defined relative to that axis. In response to determining whether user 70 has performed the critical movement or one of a plurality of critical movements, processor 730 may take appropriate steps, as described in greater detail below.

Processor 730 may be a microprocessor or other device capable of processing electronic information, including any appropriate controlling logic. Examples of processor 730 include application-specific integrated circuits (ASICs), field-programmable gate arrays (FPGAs), digital signal processors (DSPs) and any other suitable specific- or general-purpose processors. In general, processor 730 may represent one or more physically distinct components and may also provide part or all of the functionality described for sensor module 710, signal conditioning module 720, and/or feedback module 740.

Feedback module 740 may provide sensory feedback to user 70 based on a determination by processor 730 that user 70 has performed a critical movement. Feedback module 740 may include any appropriate components for providing visual, audio, tactile, or other forms of sensory feedback. Feedback module 740 may include, for example, lights, sound generators, vibrational elements, or any other components suitable for providing sensory feedback.

Memory 750 may store instructions to be executed by processor 730, movement profiles 775, user profiles 365, or any other appropriate information to be provided or used by standalone monitor 620. Memory 750 may comprise any collection and arrangement of volatile or non-volatile, local or remote devices suitable for storing data, such as for example random access memory (RAM) devices, read only memory (ROM) devices, magnetic storage devices, or any other suitable data storage devices.

User interface 760 allows user 70 to configure standalone monitor 620 and to determine the current configuration of standalone monitor 620. User interface 760 may include components that allow user 70 to configure standalone monitor 620 such as a power switch, a numberpad, a keyboard, or other types of buttons, switches, and inputs. Using user interface 760, user 70 may be able to define one or more critical movements, enter information identifying user 70, request positional information 755 stored by standalone monitor 620, and/or configure or operate standalone monitor 620 in any other suitable manner. Additionally, user interface 760 may include instrumentation that indicates the current configuration of standalone monitor 620. For example, user interface 760 may include a display indicating a particular user 70 for which standalone monitor 620 is currently configured, a counter indicating the number of times user 70 has performed the critical movement, or any other appropriate components for providing information to user 70. In general, user interface 760 may include any combination of components suitable to allow user 760 to configure and/or operate standalone monitor 620.

Data interface 770 allows other devices to provide data to or receive data from standalone monitor 620. Standalone monitor 620 may receive user profiles 365, movement profiles 775, and other information through data interface 770. Additionally, standalone monitor 620 may transmit user profiles 365, positional information 755, and other suitable data to other devices through data interface 770. In general, data interface 770 may include any components suitable to facilitate communication between standalone monitor 620 and other devices. For example, data interface 770 may represent a conventional serial port, a universal serial bus (USB) port, a wireless interface, or any other component appropriate to facilitate communication between standalone monitor 620 and other devices.

In operation, user 70 affixes position monitor 20 to user 70, grasps position monitor 20, or otherwise attaches position monitor 20 to user 70. For example, as shown in FIG. 8, position monitor 20 may include a belt or any other appropriate component for attaching position monitor 20 to user 70, such as any of those described in FIG. 3. User 70 may attach position monitor 20 to the waist of user 70. After attaching position monitor 20, user 70 or a therapist, trainer, or other party may configure position monitor 20, as described in greater detail below. After any appropriate configuration, user 70 begins movement.

During operation, sensor module 710 detects movement of user 70 based on the contents, configuration, and characteristics of sensor module 710. As indicated above, particular embodiments of standalone monitor 620 may include sensor module 710 capable of detecting rotation, translation, or any appropriate combination of the two. Additionally, particular embodiments of standalone monitor 620 may include sensor module 710 capable of detecting movement by detecting changes in a position, velocity, acceleration, and/or any other state, characteristics, or property of user 70 based on or derived from the position of user 70. Sensor module 710 generates sensor output 715 based on the detected movement and transmits sensor output to signal conditioning module 720.

Signal conditioning module 720 receives sensor output 715 and formats sensor output 715 to produce conditioned output 725 for use by processor 730 in generating positional information 755. In a particular embodiment, sensor module 710 generates sensor output 715 as an analog signal representing an angular velocity associated with the user's movement. In such an embodiment, signal conditioning module 720 may generate conditioned output 725 by integrating sensor output 715 and converting the resulting signal to a digital signal. Signal conditioning module 720 then communicates conditioned output 725 to processor 730.

Processor 730 generates positional information 755 from conditioned output 725. Processor 730 may generate positional information 755 from conditioned output 725 in any appropriate manner. Processor 730 may sum, integrate, differentiate, scale, extrapolate, interpolate, or perform any other appropriate computational and/or formatting functions to derive positional information 755 from conditioned output 125. In a particular embodiment, processor 730 may use movement described by conditioned output 725 and a previous position of user 70 or a body part of user 70 to generate positional information 755 that identifies a current position of user 70 or the relevant body part. Also, in a particular embodiment, conditioned output 725 and positional information 755 may be identical, and processor 730 may generate positional information 755 by receiving conditioned output 725.

After generating positional information 755, processor 730 then determines whether user 70 has performed a critical movement based on positional information 755. As indicated above, the critical movement may represent any predetermined movement sensor module 710 is capable of detecting. Examples of critical movement, according to particular embodiments of standalone monitor 620, may include user 70 improperly using his or her back during lifting, extending an injured limb beyond a safe range of motion, using proper form for a golf swing, or any other movement that user 70 desires to encourage, discourage, and/or monitor.

Processor 730 may determine whether user 70 has performed a critical motion in any suitable manner. Particular embodiments of standalone monitor 620 store a movement profile 775 in memory 750. Movement profile 775 includes data describing a particular critical movement. Processor 730 may determine whether user 70 has performed a critical movement by comparing positional information 755 to data stored in movement profile 775. Particular embodiments of standalone monitor 620 may be configured to recognize multiple critical movements. As a result, standalone monitor 620 may be configured to store one or more movement profiles 775 and processor 730 may determine whether user 70 has performed a critical movement by comparing positional information 755 to data stored in one or more of movement profiles 775.

If processor 730 determines that user 70 has performed a critical motion, processor 730 may communicate this determination to feedback module 740. Feedback module 740 may then provide sensory feedback to user 70. For example, if processor 730 indicates that user 70 has performed a critical movement, feedback module 740 may flash lights, generate sound, vibrate standalone monitor 620, or provide any other appropriate form of sensory feedback.

Additionally or alternatively, if processor 730 determines that user 70 has performed a critical motion, processor 730 may store positional information 755 or other appropriate data to memory 750. For example, processor 730 may maintain a count, in memory 750, of a number of times that user 70 has performed a critical motion. Processor 750 may increment the count as a result of determining that user 70 has performed a critical motion.

Furthermore, if processor 750 is capable of detecting multiple critical motions, processor 750 may determine an appropriate action to take based on the particular critical motion detected. As one example, processor 750 may provide different types of sensory feedback based on the particular critical motion detected by standalone monitor 620. As another alternative processor 750 may maintain separate counts for each critical motion and may increment the appropriate counter in response to detecting a particular critical motion.

Prior to operation or at any other appropriate time, user 70 may configure standalone monitor 620. User 70 may configure standalone monitor by loading configuration information through data interface 770, receiving input from user 70 through user interface 760, or by taking any other appropriate steps to prepare standalone monitor 620 for use. As one example, user 70 may load, through data interface 770, movement profile 775 that identifies a critical motion for user 70. As another example, user 70 may reset a count stored in memory 750. As another example, user 70 may store movement profile 775 by performing a critical motion while wearing or holding standalone monitor 620. In general, use 70 may configure standalone monitor 620 in any appropriate manner. As another example, user 70 may load from memory 750 a user profile 365 associated with user 70 that identifies multiple movement profiles 775 associated with user 70.

In a particular embodiment, user 70 or another appropriate party may be able download or retrieve information from standalone monitor 620 after use or at any other appropriate time. For example, user 70 may download a log of critical motion performed by user 70 while wearing standalone monitor 620. As another example, user 70 may be able to read a display of user interface 760 to determine the count of critical motions performed by user 70.

Figure 9:
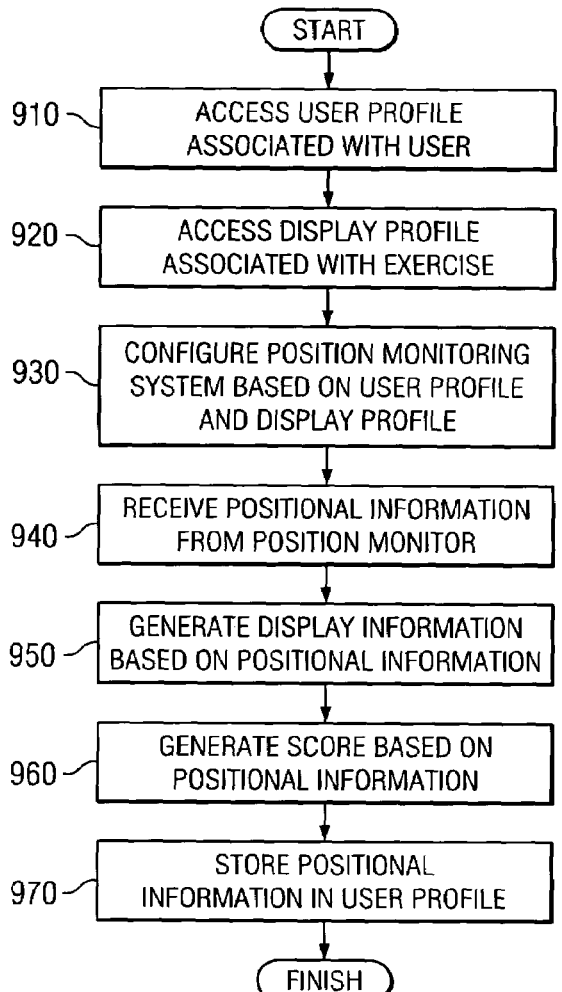
FIG. 9 is a flow chart illustrating operation of a particular embodiment of the display generator according to a particular embodiment.

FIG. 9 is a flowchart illustrating operation of display generator 40 according to a particular embodiment. At step 910, display generator 40 accesses a user profile 365 associated with user 70. User profile 365 may specify an exercise to be performed by user 70. Thus, at step 920, display generator 40 may access display profile 375 associated with an exercise to be performed by user 70. At step 930, display generator 40 may configure position monitoring system 10 based on user profile 365 and display profile 375.

At step 940, display generator 40 may begin receiving positional information 55 from position monitor 20 through receiver 40, describing movement of user 70 associated with an exercise performed by the user. Display generator 40 begins generating display information based on positional information 55. Display generator 40 may also generate the display information based on, for example, information from user profile 365 and display profiles 375 at step 950. At step 960, display generator 40 generates score 90 rating the performance of user 70 based on positional information 55 and/or information included in user profile 365 and display profiles 375. Display generator 40 may then store positional information 55 and/or other information describing movement or performance of user 70 in user profile 365 at step 970.

Figure 10:
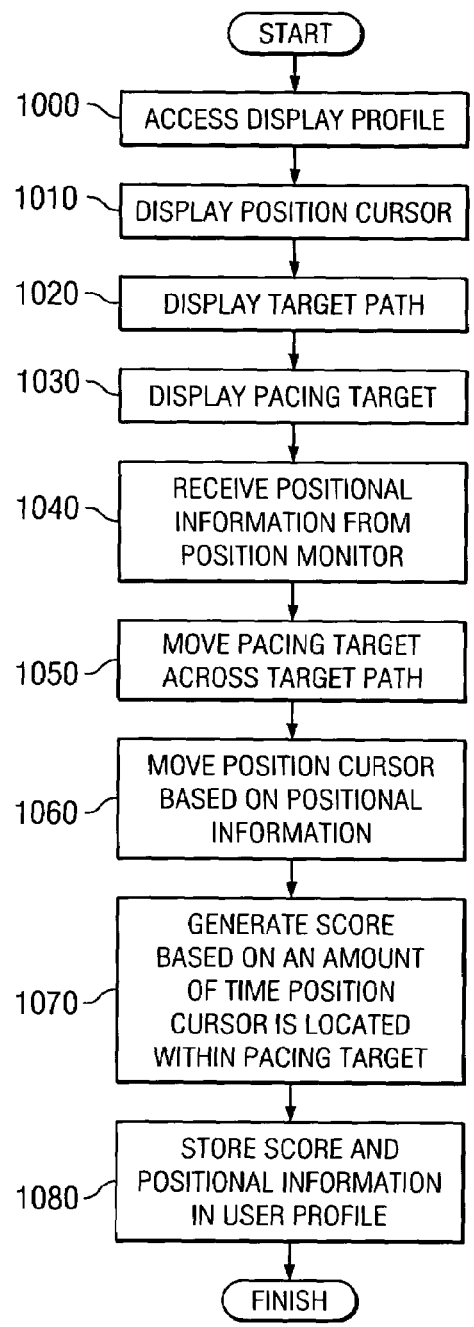
FIG. 10 is a flow chart illustrating operation of the display, according to a particular embodiment, while the monitoring system operates in a particular display mode.

FIG. 10 is a flowchart illustrating operation of display generator 40 while operating in the monitor mode, according to a particular embodiment. During operation of the described embodiment of display generator 40, user 70 moves position cursor 310 with a goal of mimicking the movement of pacing cursor 340. At step 1000, display generator 40 accesses display profile 375 that includes exercise parameters. Display generator 40 displays position cursor 310 at step 1010.

Display generator 40 displays a target path that describes an exercise goal associated with the exercise at step 1020 based on the exercise parameters in display profile 375. At step 1030, display generator 40 displays pacing target 340.

At step 1040, display generator 40 begins receiving positional information 55 from position monitor 20. Display generator 40 moves pacing target 340 across target path 320 defining a desired movement associated with an exercise performed by user 70 at step 1050. At step 1060, display generator 40 moves position cursor 310 based on positional information 55 received from position monitor 20 affixed to user 70. Positional information 55 describes movement associated with the exercise performed by user 70. Display generator 40 generates score 90 based on an amount of time position cursor 310 is located within pacing target 340 at step 1070. At step 1080, display generator 40 stores score 90 and positional information 55 in a particular user profile 365 associated with user 70.

Figure 11:
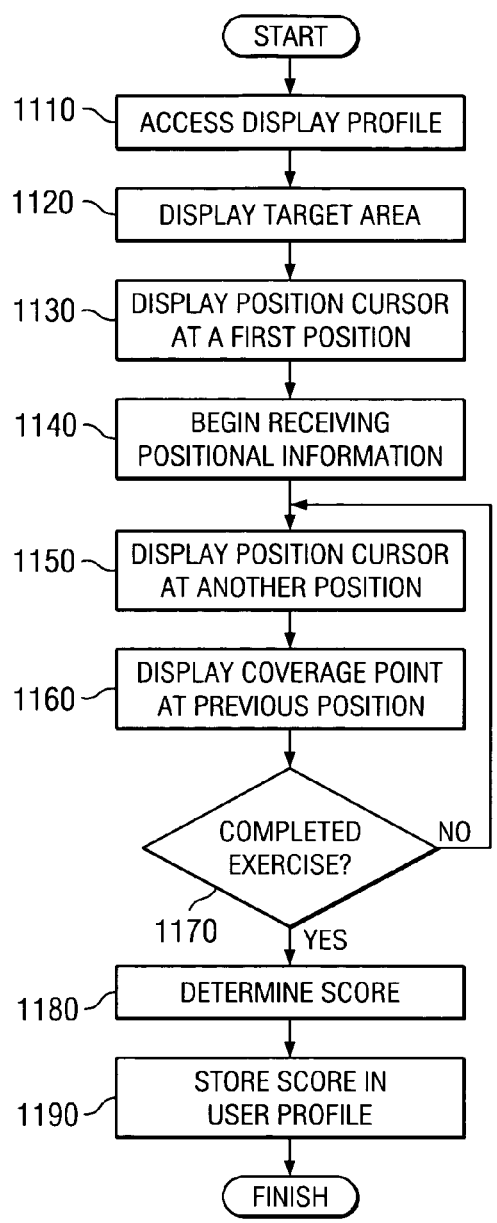
FIG. 11 is a flow chart illustrating operation of the display, according to a particular embodiment, while the monitoring system operates in a particular display mode.

FIG. 11 is a flowchart illustrating operation of display generator 40 while operating in the coverage mode, according to a particular embodiment. During operation of the described embodiment of display generator 40, user 70 performs an exercise with a goal of moving position cursor 410 through a range of motion defined by target area 420. At step 1110, display generator 40 accesses display profile 375 that defines a boundary or other characteristics of target area 420. Target area 420 is associated with an exercise goal of an exercise to be performed by user 70. At step 1120, display generator 40 displays target area 420.

Display generator 40 displays position cursor 410 at a first position within target area 420 at step 1130. At step 1140, display generator begins receiving positional information 55 from position monitor 20. At step 1150, display generator 40 displays position cursor 410 at another position within target area 420 based on positional information 55 describing a movement of user 70. Additionally, display generator 40 displays coverage point 430 at the previous position, indicating that the movement of the user has covered the first position at step 1160.

At step 1170, display generator 40 determines whether user 70 has completed the exercise. Display generator 40 may determine that user 70 has completed the exercise based on a time limit associated with the exercise, based on lack of movement on the part of user 70, or any other appropriate considerations. If display generator 40 determines that user 70 has not completed the exercise, operation of display generator 40 returns to step 1150. If display generator 40 determines that user 70 has completed the exercise, display generator 40 determines score 90 based on a portion of target area 420 covered by coverage points 430 at step 1180. At step 1190, display generator 40, stores score 90 in a particular user profile 365 associated with user 70.

Figure 12:
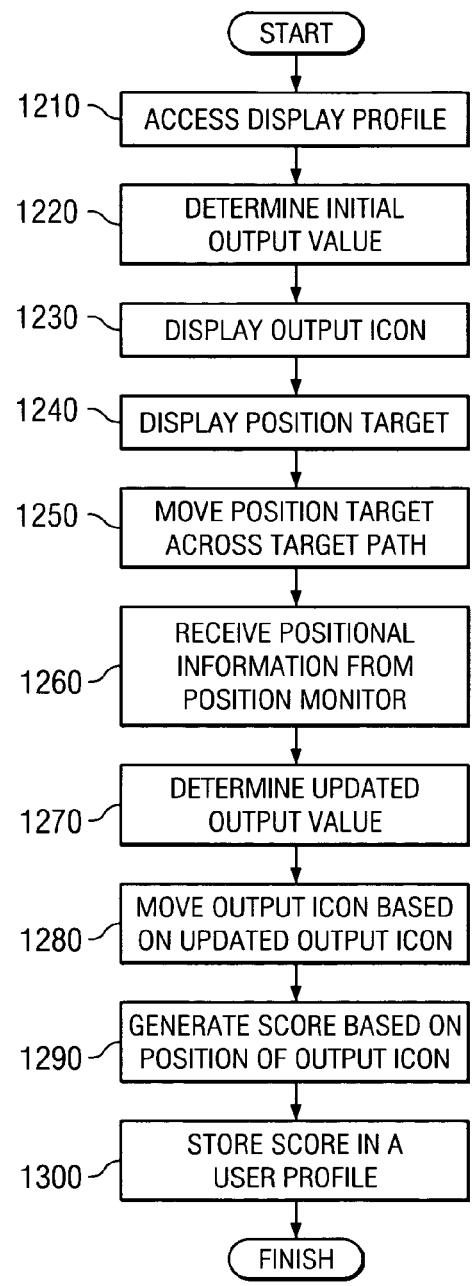
FIG. 12 is a flow chart illustrating operation of the display, according to a particular embodiment, while the monitoring system operates in a particular display mode.

FIG. 12 is a flowchart illustrating operation of display generator 40 while operating in the coverage mode, according to a particular embodiment. During operation of the described embodiment of display generator 40, user 70 performs an exercise with a goal of moving position cursor 410 through a range of motion defined by target area 420. During operation of the described embodiment of display generator 40, user 70, as part of performing an exercise, moves output icon 510 with a goal of mimicking the movement of position target 520.

At step 1210 display generator accesses display profile 375 that describes an exercise to be performed and includes model parameters. Display generator 40 then determines an initial output value of a naturally unstable system based on the model parameters at step 1220. Display generator 40 displays output icon 510 at a position determined based on the initial output value at step 1230. At step 1240, display generator 40 displays position target 520.

At step 1250, display generator begins moving position target 520 across a target path defining a desired movement associated with the exercise performed by user 70. At step 1260, display generator 40 begins receiving positional information 55 from position monitor 20 describing movement of user 70 as user 70 performs the exercise. Position generator 40 determines an updated output value of the naturally unstable system based on positional information 55 and the model parameters at step 1270. At step 1280, display generator 40 moves output icon 510 based on the updated output value.

At step 1290, display generator 40 generates score 90 based in part on the position of output icon 510. For example, display generator 40 may generate score 90 based on an amount of time the position of output icon 510 is located within position target 520. At step 1300, display generator 40 stores score 90 in a particular user profile 365 associated with user 70.

Figure 13:
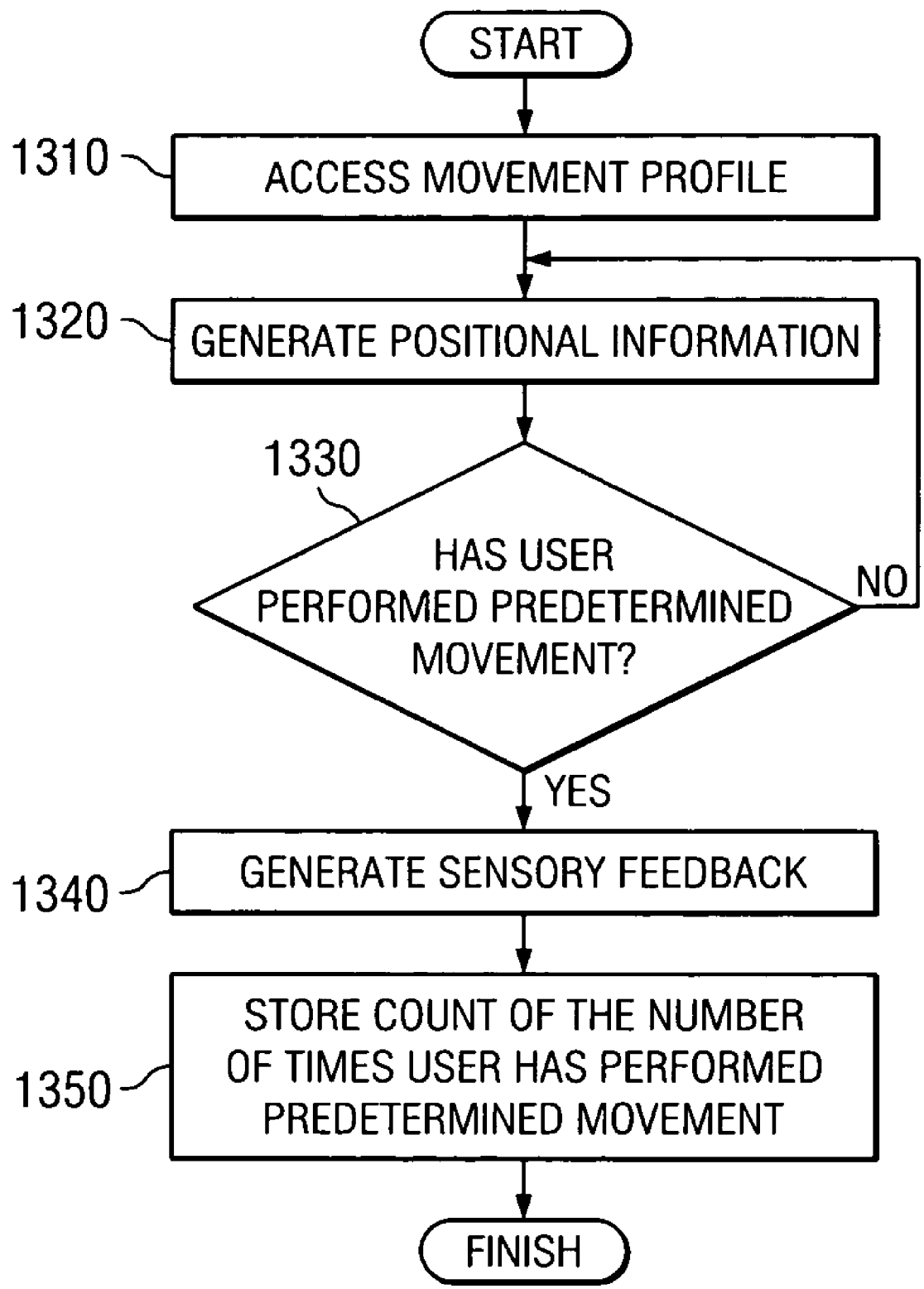
FIG. 13 is a flow chart illustrating operation of a particular embodiment of the standalone position monitor.

FIG. 13 is a flowchart illustrating operation of standalone monitor 620, according to a particular embodiment. At step 1310, standalone monitor 620 accesses a movement profile 775 that includes information describing a predetermined movement. At step 1320, standalone monitor 620 begins generating positional information 755 describing a movement of user 70.

At step 1330, standalone monitor 620 determines whether user 70 has performed the predetermined movement based on positional information 755. If standalone monitor 620 determines that user 70 has not performed the predetermined movement, operation returns to step 1320. If standalone monitor 620 determines that user 70 has performed the predetermined movement, standalone monitor 620 generates sensory feedback indicating that user 70 has performed the predetermined movement at step 1330. At step 1340, standalone monitor 620 may store positional information 755. Standalone monitor 620 may also store a count of a number of times the user performs the predetermined movement at step 1350. Depending on the configuration of standalone monitor 620, standalone monitor 620 may then repeat the process by returning to step 1320.

Although the present invention has been described with several embodiments, a myriad of changes, variations, alterations, transformations, and modifications may be suggested to one skilled in the art, and it is intended that the present invention encompass such changes, variations, alterations, transformations, and modifications as fall within the scope of the appended claims. For example, in alternative embodiments, position monitor 20 may be capable of operating from a stationary position. More specifically, position monitor 20 may include one or more optical transmitters and optical sensors capable of detecting movement of an appropriately positioned user 70. In such an embodiment, position monitor 20 may be capable of operating effectively without being attached to user 70 or maintaining physical contact with user 70. Thus, more generally while particular embodiments of monitoring system 10 and standalone monitor 620 are described and illustrated, monitoring system 10 and standalone monitor 620 each contemplate any suitable combination and arrangement of components for monitoring position and/or movement of user 70 and providing sensory feedback based on the user's position and/or movement.

What is claimed is:

1. A device for monitoring a movement of a user, comprising:
    a sensor module operable to generate positional information, the positional information describing a movement of a portion of a user's body relative to one of the user's joints;
    a processor operable to:
        receive positional information from the sensor module;
        compare the received positional information to stored positional information; and
        determine based on a comparison of the received positional information and the stored positional information that the user has performed a predetermined movement;
    a feedback module operable to generate sensory feedback in response to determining that the user has performed the predetermined movement; and
    a housing enclosing at least a portion of each of the sensor module, the processor, and the feedback module.

2. The device of claim 1, wherein the sensor module is further operable to generate positional information based on an angular difference associated with a motion of the user.

3. The device of claim 1, further comprising a memory operable to store the received positional information.

4. The device of claim 3, wherein the memory is operable to store the received positional information by storing a count of a number of times the user performs the predetermined movement.

5. The device of claim 3, wherein the memory is further operable to store a plurality of user profiles associated with a plurality of users and wherein the memory is further operable to store the received positional information by storing the received positional information in a user profile associated with a current user.

6. The device of claim 3, wherein the memory is operable to store a plurality of movement profiles, each movement profile containing stored positional information associated with a particular predetermined movement, and wherein the processor is further operable to determine that the user has performed the predetermined movement by:
    identifying a movement profile associated with an exercise being performed by the user; and
    comparing the generated positional information with stored positional information from the identified movement profile.

7. The device of claim 3, wherein the processor is further operable to generate the stored positional information by:
    receiving model positional information associated with the predetermined movement from the sensor module;
    storing the model positional information associated with the predetermined movement.

8. The device of claim 1, further comprising a belt coupled to the housing, the belt operable to attach the housing to the user.

9. The device of claim 1, further comprising one or more fastening straps coupled to the housing, the fastening straps operable to attach the housing to the user.

10. The device of claim 1, further comprising a sleeve, the sleeve comprising a pocket, the pocket operable to hold the housing while the user exercises, and wherein the housing is further operable to be removed from the pocket.

11. The device of claim 1, wherein the feedback module is operable to generate sensory feedback by generating one or more of visual, audio or tactile feedback.

12. A method for monitoring a movement of a user, comprising:
    generating positional information at a sensor module enclosed at least in part by a housing, the positional information describing a movement of a portion of a user's body relative to one of the user's joints;
    receiving the generated positional information at a processor enclosed at least in part by the housing;
    comparing the generated positional information to stored positional information using the processor;

determining based on a comparison of the generated positional information and the stored positional information that the current user has performed a predetermined movement; and generating sensory feedback with a feedback module in response to determining that the current user has performed the predetermined movement, the feedback module enclosed at least in part by the housing.

13. The method of claim 12, wherein generating positional information comprises generating positional information based on an angular difference associated with a motion of the user.

14. The method of claim 12, further comprising storing a count of a number of times the user performs the predetermined movement.

15. The method of claim 12, further comprising:
storing a plurality of movement profiles;
identifying a movement profile associated with an exercise being performed by the user, and wherein comparing the generated positional information to stored positional information comprises comparing the generated positional information with stored positional information from the identified movement profile.

16. The method of claim 12, wherein generating positional information comprises:
generating positional information associated with the predetermined movement;
storing the positional information associated with the predetermined movement; and
generating positional information associated with a user movement; and wherein the processor is further operable to determine whether the user has performed the predetermined movement by comparing the positional information associated with the user movement with the positional information associated with the predetermined movement.

17. The method of claim 12, wherein generating sensory feedback comprises generating one or more of visual, audio or tactile feedback.

18. A system for monitoring a movement of a user, the system comprising:
means for generating positional information associated with a portion of a user's body relative to one of the user's joints;
means for comparing the generated positional information to stored positional information;
means for determining based on a comparison of the generated positional information and the stored positional information that the current user has performed a predetermined movement;
means for generating sensory feedback in response to determining that the current user has performed the predetermined movement; and
housing means enclosing at least a portion of each of the means for generating positional information, the means for comparing, and the means for generating sensory feedback.

19. A method for monitoring a movement of a user, comprising:
generating positional information at a sensor module enclosed at least in part by a housing, the positional information describing a movement of a portion of a user's body relative to one of the user's joints;
receiving the generated positional information at a processor enclosed at least in part by the housing;
comparing the generated positional information to stored positional information using the processor;
determining based on a comparison of the generated positional information and the stored positional information that the user has performed a predetermined movement;
generating sensory feedback with a feedback module in response to determining that the user has performed the predetermined movement, the feedback module enclosed at least in part by the housing; and
storing a count of a number of times the user performs the predetermined movement.

20. The device of claim 1, wherein the housing comprises a handle, the handle operable to hold resistive elements, and wherein the motion sensor is operable to detect movement associated with resistance training.

21. The device of claim 1, wherein the processor is operable to compare the received positional information to stored positional information by comparing the received positional information to stored positional information associated with a therapeutic exercise.

22. The device of claim 1, wherein the processor is operable to compare the received positional information to stored positional information by comparing the received positional information to stored positional information associated with a movement to be learned by the user.

23. The method of claim 12, wherein comparing the generated positional information to stored positional information comprises comparing the generated positional information to stored positional information associated with a therapeutic exercise.

24. The method of claim 12, wherein comparing the generated positional information to stored positional information comprises comparing the generated positional information to stored positional information associated with a movement to be learned by the user.

25. The method of claim 12, further comprising:
identifying one of a plurality of stored user profiles that is associated with a current user; and
storing the generated positional information in a user profile associated with the current user.

26. The system of claim 18, further comprising:
means for identifying one of a plurality of stored user profiles that is associated with a current user; and
means for storing the generated positional information in a user profile associated with the current user.

* * * * *